US008721550B2

(12) United States Patent
Oguzman et al.

(10) Patent No.: US 8,721,550 B2
(45) Date of Patent: *May 13, 2014

(54) HIGH VOLTAGE ULTRASOUND TRANSMITTER WITH SYMMETRICAL HIGH AND LOW SIDE DRIVERS COMPRISING STACKED TRANSISTORS AND FAST DISCHARGE

(75) Inventors: Ismail H. Oguzman, Plano, TX (US); Arash Loloee, Allen, TX (US); Myron J. Koen, Tucson, AZ (US)

(73) Assignee: Texas Instruments Incorporated, Dallas, TX (US)

( * ) Notice: Subject to any disclaimer, the term of this patent is extended or adjusted under 35 U.S.C. 154(b) by 927 days.

This patent is subject to a terminal disclaimer.

(21) Appl. No.: 12/261,269

(22) Filed: Oct. 30, 2008

(65) Prior Publication Data

US 2010/0113936 A1    May 6, 2010

(51) Int. Cl.
*A61B 8/14* (2006.01)

(52) U.S. Cl.
USPC .......................................................... 600/459

(58) Field of Classification Search
CPC .................................................... B06B 1/0215
USPC ....... 310/334; 326/83, 84; 327/108; 600/437, 600/443, 459
See application file for complete search history.

(56) References Cited

U.S. PATENT DOCUMENTS

| | | | | |
|---|---|---|---|---|
| 3,984,703 A * | 10/1976 | Jorgensen | ................... | 327/206 |
| 4,044,297 A * | 8/1977 | Nobue et al. | ................... | 323/271 |
| 4,163,908 A * | 8/1979 | Price | ........................... | 327/540 |
| 4,456,837 A * | 6/1984 | Schade, Jr. | ..................... | 327/259 |
| 4,486,670 A * | 12/1984 | Chan et al. | ..................... | 326/81 |
| 4,563,595 A * | 1/1986 | Bose | ............................ | 327/206 |
| 4,634,993 A * | 1/1987 | Koen | ........................... | 330/253 |
| 4,686,511 A * | 8/1987 | Koen | ........................... | 341/118 |
| 4,763,107 A * | 8/1988 | Koen et al. | ..................... | 341/156 |
| 5,030,853 A * | 7/1991 | Vinal | ............................ | 326/84 |
| 5,880,618 A * | 3/1999 | Koen | ........................... | 327/351 |
| 6,118,340 A * | 9/2000 | Koen | ........................... | 330/253 |
| 6,135,961 A | 10/2000 | Pflugrath et al. | | |
| 6,144,223 A * | 11/2000 | Momtaz | ...................... | 326/83 |
| 6,218,765 B1 * | 4/2001 | Kawabe | ...................... | 310/317 |
| 6,229,375 B1 * | 5/2001 | Koen | ........................... | 327/351 |
| 6,380,766 B2 * | 4/2002 | Savord | ......................... | 327/108 |
| 6,642,795 B2 * | 11/2003 | Koen et al. | ..................... | 330/298 |
| 6,648,826 B2 | 11/2003 | Little et al. | | |

(Continued)

OTHER PUBLICATIONS

MD1812, Supertex, Mar. 17, 2006.*

(Continued)

*Primary Examiner* — Unsu Jung
*Assistant Examiner* — Serkan Akar
(74) *Attorney, Agent, or Firm* — Alan A. R. Cooper; W. James Brady, III; Frederick J. Telecky, Jr.

(57) ABSTRACT

A system and method for providing a high voltage ultrasonic drive signal from an ultrasound transmitter are disclosed herein. An ultrasound transmitter includes a first driver and a bias network. The first driver includes a first plurality of drive transistors that when activated drive an ultrasound transmitter output to a first voltage. The first bias network is coupled to the first plurality of drive transistors, and, at least in part, controls distribution, across the drive transistors, of voltage at the ultrasound transmitter output. Control inputs of the first driver are decoupled from the ultrasound transmitter output.

15 Claims, 2 Drawing Sheets

(56) References Cited

U.S. PATENT DOCUMENTS

| | | | |
|---|---|---|---|
| 6,705,995 B1* | 3/2004 | Poland et al. | 600/447 |
| 6,856,175 B2* | 2/2005 | Wodnicki | 327/108 |
| 6,864,702 B1* | 3/2005 | Teggatz et al. | 324/762.09 |
| 6,998,898 B2* | 2/2006 | Koen | 327/309 |
| 7,064,607 B2* | 6/2006 | Maclean et al. | 330/136 |
| 7,071,664 B1* | 7/2006 | Teggatz et al. | 323/280 |
| 7,071,740 B2* | 7/2006 | Adams et al. | 327/110 |
| 7,135,920 B2* | 11/2006 | Koen et al. | 330/69 |
| 7,151,409 B2* | 12/2006 | Koen et al. | 330/254 |
| 7,280,330 B2* | 10/2007 | Oguzman et al. | 361/56 |
| 7,304,415 B2* | 12/2007 | Petersen et al. | 310/334 |
| 7,314,445 B2* | 1/2008 | Wodnicki et al. | 600/437 |
| 7,521,980 B2* | 4/2009 | Koen | 327/308 |
| 7,604,596 B2 | 10/2009 | Hwang et al. | |
| 7,705,517 B1* | 4/2010 | Koen et al. | 310/317 |
| 7,794,400 B2* | 9/2010 | Phelps et al. | 600/459 |
| 2003/0151417 A1* | 8/2003 | Koen | 324/673 |
| 2003/0151462 A1* | 8/2003 | Koen et al. | 330/298 |
| 2003/0163047 A1 | 8/2003 | Little et al. | |
| 2004/0113669 A1* | 6/2004 | Wodnicki | 327/170 |
| 2004/0133110 A1 | 7/2004 | Little et al. | |
| 2004/0259505 A1* | 12/2004 | Vasanth | 455/78 |
| 2005/0140425 A1* | 6/2005 | Adams et al. | 327/427 |
| 2005/0140437 A1* | 6/2005 | Maclean et al. | 330/136 |
| 2005/0265267 A1 | 12/2005 | Hwang | |
| 2006/0017506 A1* | 1/2006 | Koen et al. | 330/254 |
| 2006/0044058 A1* | 3/2006 | Koen et al. | 330/69 |
| 2006/0050452 A1* | 3/2006 | Oguzman et al. | 361/56 |
| 2006/0052697 A1* | 3/2006 | Hossack et al. | 600/437 |
| 2006/0132108 A1* | 6/2006 | Teggatz et al. | 323/282 |
| 2006/0220734 A1* | 10/2006 | Koen | 330/9 |
| 2007/0090857 A1* | 4/2007 | Shau | 326/81 |
| 2008/0048751 A1* | 2/2008 | Koen | 327/308 |
| 2008/0262357 A1* | 10/2008 | Wodnicki | 600/459 |
| 2008/0316659 A1* | 12/2008 | Oguzman et al. | 361/56 |
| 2009/0251025 A1* | 10/2009 | Kondou et al. | 310/316.01 |
| 2010/0012119 A1 | 1/2010 | Sallak et al. | |
| 2010/0113935 A1* | 5/2010 | Koen et al. | 600/459 |

OTHER PUBLICATIONS

MD1711, Supertex, Jun. 28, 2006.*

B. Haider, "Power Drive Circuits for Medical Diagnostic Medical Ultrasound," IEEE Proceedings of the 18th international Symposium on Power Semiconductor Devices and ICs, Jun. 2006.

M. A. Averkiou, D. N. Roundhill and J. E. Powers, "A New Imaging Technique Based on the Nonlinear Properties of Tissues," IEEE Ultrasonics Symposium, 1997.

B. Haider and R. Y. Chiao, "Higher Order Nonlinear Ultrasonic Imaging," IEEE Ultrasonics Symposium, 1999.

* cited by examiner

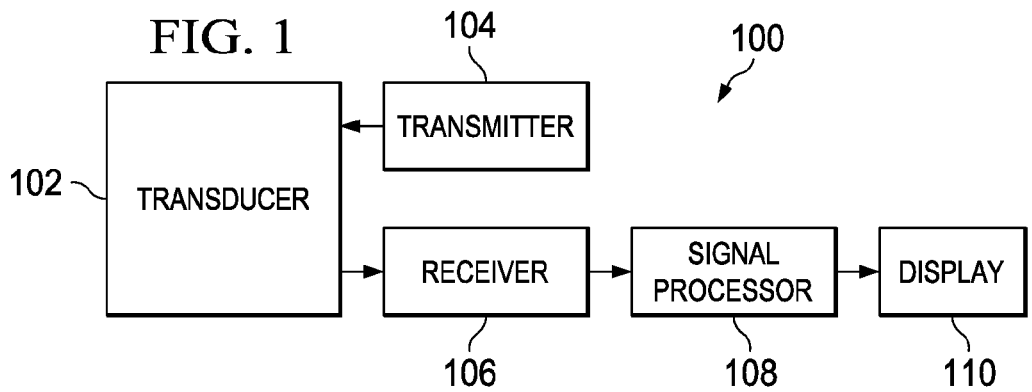
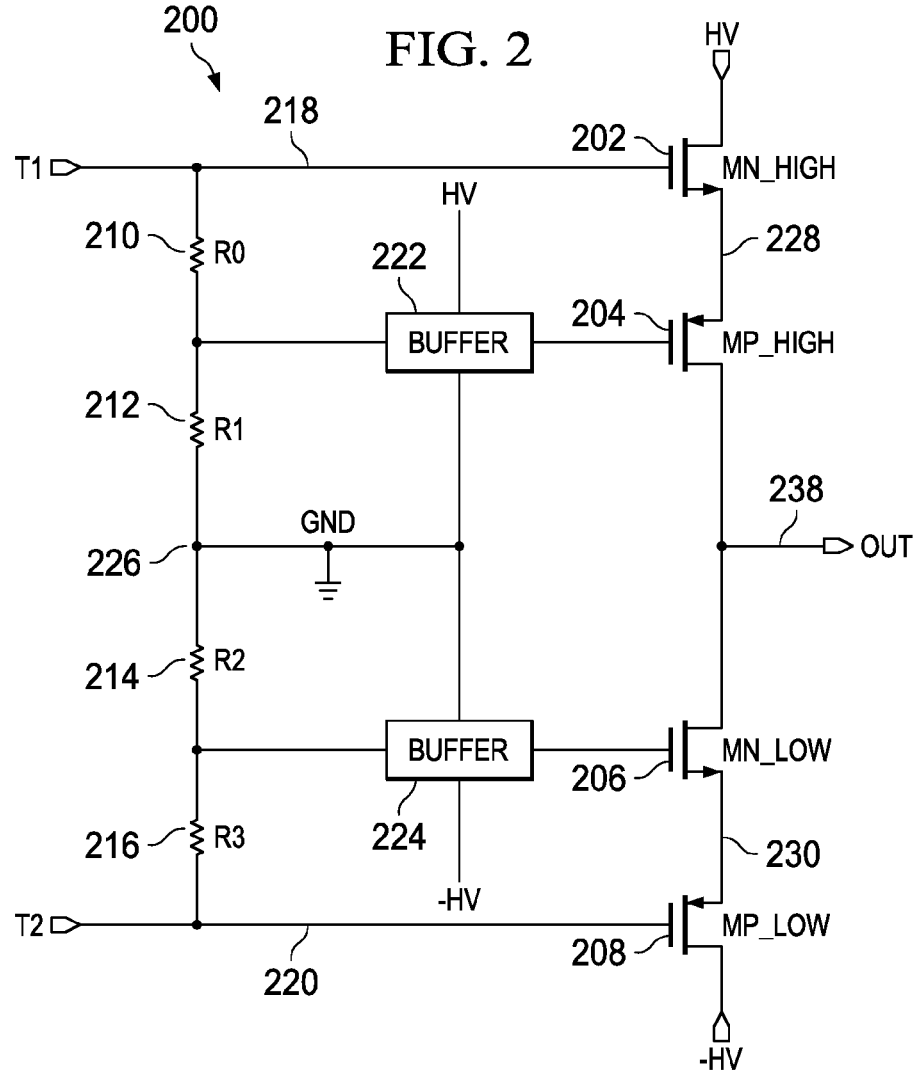

HIGH VOLTAGE ULTRASOUND TRANSMITTER WITH SYMMETRICAL HIGH AND LOW SIDE DRIVERS COMPRISING STACKED TRANSISTORS AND FAST DISCHARGE

CROSS REFERENCE TO RELATED APPLICATIONS

This application contains subject matter that may be related to U.S. patent application Ser. No. 12/261,185, entitled "Low Power Continuous Wave Ultrasound Transmitter", U.S. patent application Ser. No. 12/261,209, entitled "Ultrasound Transmitter", and U.S. patent application Ser. No. 12/261,252, entitled "Ultrasound Transmitter".

BACKGROUND

Ultrasonic imaging has become a widely used tool in medical applications. Ultrasound techniques introduce high-frequency acoustic waves into a subject's body. The received echoes of those waves provide information allowing a trained observer to view the subject's internal organs. Ultrasound imaging equipment uses transducers that convert electrical energy into acoustic energy. Piezo-electric crystals are one commonly used type of electrical to acoustical transducer. To obtain a clear image, a high signal to noise ratio is desirable to overcome random noise associated with the imaging process. One way to increase the signal-to-noise ratio is to increase the amplitude of the signal driving the transducer. Generally, the transducer drive signal may require voltages in the range of ±75 volts to ±100 volts.

There are two broad categories of ultrasound transmitters, digital and analog. The analog type takes a signal generated digitally and after being converted to analog form, by a digital-to-analog converter, the signal is amplified to the required higher voltage by a power amplifier. This type of transmitter is capable of generating complex waveforms by using a high-resolution digital-to-analog converter with a resolution of, for example, 12 bits. This technique is expensive and finds application in high-end ultrasound imaging systems.

Digital transmitters are simpler and less expensive than analog transmitters. Unfortunately, the semiconductor process technologies used to fabricate digital circuits, which are often less expensive and provide better performance than high voltage processes, do not typically accommodate the high voltages required to produce an acceptable signal-to-noise ratio in an ultrasound imager. Furthermore, users of ultrasound imaging systems demand both power efficiency and portability in modern ultrasound equipment.

SUMMARY

Various systems and methods for implementing a high-voltage ultrasound transmitter are disclosed herein. In accordance with at least some embodiments, an ultrasound transmitter includes a first driver and a first bias network. The first driver includes a first plurality of drive transistors that when activated drive an ultrasound transmitter output to a first voltage. The first bias network is coupled to the first plurality of drive transistors. The first bias network, controls, at least in part, distribution across the drive transistors of voltage at the ultrasound transmitter output. Control inputs of the first driver are decoupled from the ultrasound transmitter output.

In accordance with at least some other embodiments, an ultrasound imaging system includes a receiver and a transmitter. The receiver receives detected ultrasonic signals. The transmitter drives a transducer that converts electrical signals into acoustic signals. The transmitter includes a high-side driver, a low-side driver, and a bias network. The high-side driver drives a transmitter output to a positive voltage. The low-side driver drives the transmitter output to a negative voltage. The bias network substantially equalizes the voltage across drive transistors of each of the high-side driver and the low-side driver. A node of the bias network is connected to ground.

In accordance with yet other embodiments, an ultrasound transmitter includes a plurality of drive transistors that drive a transmitter output. The transmitter further includes means for decoupling the control inputs of the plurality of drive transistors from the transmitter output.

BRIEF DESCRIPTION OF THE DRAWINGS

For a detailed description of exemplary embodiments of the invention, reference will now be made to the accompanying drawings in which:

FIG. 1 shows a block diagram of an exemplary ultrasound imaging system in accordance with various embodiments;

FIG. 2 shows an exemplary ultrasound transmitter circuit that employs a symmetrical output configuration and provides fast output signal zeroing without a clamp circuit in accordance with various embodiments.

NOTATION AND NOMENCLATURE

Figure 3:
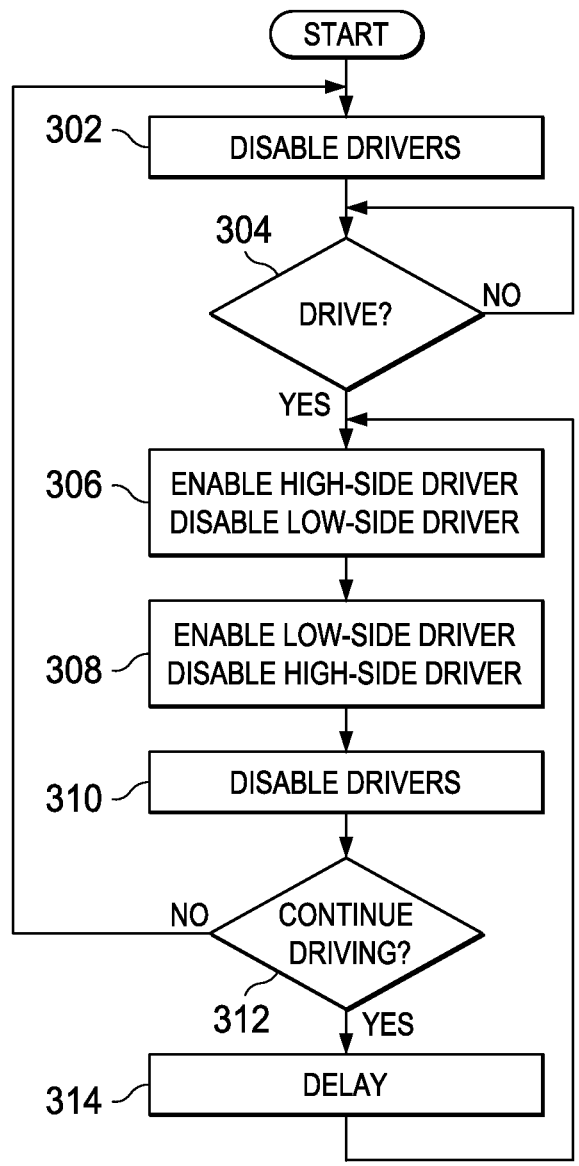
FIG. 3 shows a flow diagram for a method for generating a high voltage ultrasonic drive signal in accordance with various embodiments.

Certain terms are used throughout the following description and claims to refer to particular system components. As one skilled in the art will appreciate, companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct electrical connection. Thus, if a first device couples to a second device, that connection may be through a direct electrical connection, or through an indirect electrical connection via other devices and connections.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

The performance and cost efficiency of low-voltage semiconductor processes make it desirable to use those processes to implement high-voltage circuits. High-voltage circuits can be so implemented by connecting transistors (e.g., field effect transistors ("FETs")) in series (i.e., stacked), and in such a way as to ensure that the voltage across the transistors is distributed in a predictable manner. If transistors are stacked without considering voltage distribution, it may be possible for the voltage across an individual transistor to exceed the process specification. Moreover, a bias network that achieves predictable voltage distribution can result in undesirable power dissipation and/or poor switching performance. Drivers employing stacked transistors can also suffer from an undesirable lack of output symmetry due to process and/or temperature variations. Further, to reduce power dissipation, a low on resistance is needed, requiring the stacked transistors to be large.

Moreover, in order to produce a compact ultrasound imaging system and a low cost, it is desirable to reduce the area consumed by the ultrasonic transmitters. Embodiments of the present disclosure employ symmetrically configured high-side and low-side drivers wherein each driver includes serially connected complementary transistors (i.e., an N-type transistor in series with a P-type transistor in each of the high and low side drivers). Additionally, embodiments of the present disclosure are configured to quickly return the transmitter output to zero when the transmitter is disabled. Embodiments achieve quick return to zero while avoiding a dedicated clamping circuit. Such features advantageously reduce circuit area, provide improved performance across process and temperature, and result in reduced transmitter quiescent power dissipation.

FIG. 1 shows a block diagram of an exemplary ultrasound imaging system 100 in accordance with various embodiments. The terms "ultrasound" or "ultrasonic" generally refer to acoustic waves at frequencies beyond the range of human hearing (e.g., frequencies above 20 KHz). The system 100 comprises a transducer 102, a transmitter 104, a receiver 106, a signal processor 108, and a display 110. The transducer 102 converts the electrical drive signals generated by the transmitter 104 into sound waves (i.e., pressure waves) that are introduced into the subject to be imaged, for example, a human body when considering medical ultrasound. The transducer 102 can comprise a piezoelectric crystal, electromagnetic transducer, micro-electro-mechanical system ("MEMS") transducer or other device that converts an electrical signal into sound waves. Moreover, the transducer 102 can comprise one or more transducer elements. The transducer 102 also detects ultrasonic waves reflected by internal structures of the subject and converts the detected waves into electrical signals. In some embodiments, the same transducer elements are used to generate ultrasonic waves and to detect ultrasonic waves. In other embodiments, separate transducer elements are used for wave generation and detection.

The transmitter 104 is coupled to the transducer 102. The transmitter 104 produces an oscillating electrical signal at a frequency and amplitude suitable for imaging desired structures internal to the subject. For example, transmitter output signals for use in imaging the internal organs of a human body may range in frequency from 1 to 20 megahertz with lower frequencies providing lower resolution and greater imaging depth. Other applications may use different frequencies. The transmitter 104, while not limited to any particular signal amplitudes, may provide, for example, a drive signal amplitude in the range of ±75 volts. The transmitter 104 employed in embodiments of the present disclosure advantageously uses transmitter circuitry that allows for efficient implementation of a high voltage ultrasonic driver on a low voltage semiconductor process, while reducing circuit area and power dissipation, and improving performance across temperature and process variation. Embodiments employ a variety of novel means to reduce circuit area, for example, embodiments of the present disclosure are configured to eliminate the need for a dedicated transmitter output clamping circuit.

The receiver 106 is coupled to the transducer 102. As explained above, the transducer 102 detects ultrasonic waves reflected by subject internal structures. The transducer 102 converts the detected waves into electrical signals. The electrical signals are provided to the receiver 106. The receiver 106 performs initial processing of the received signals. Processing performed by the receiver 106 can comprise, for example, amplifying, filtering, digitizing, etc.

The signal processor 108 is coupled to the receiver 106. The signal processor 108 may, for example, provide post-digitization filtering of received signals, detect signal reflections, and prepare output signals for display on the display 110. The signal processor 108 may comprise, for example, a digital signal processor or other microprocessor or microcomputer and associated software programming along with attendant memory and interface devices, or dedicated hardware circuitry adapted to perform the processing functions. The display 110 may be a liquid crystal display, a cathode ray display, or any other suitable display device.

FIG. 2 shows an exemplary ultrasound transmitter circuit 200 that employs a symmetrical output configuration and provides fast output signal zeroing without an output clamping circuit in accordance with various embodiments. The transmitter 200 is configured to provide symmetry between the high side and the low side of the transmitter 200 output circuitry. Accordingly, the high side driver and the low side driver each include both a P-type transistor and an N-type transistor. The high-side driver comprises N-type transistor MN_HIGH 202 and P-type transistor MP_HIGH 204 connected in series, and the low-side driver comprises N-type transistor MN_LOW 206 and P-type transistor MP_LOW 208 connected in series. When enabled, stacked drive transistors MN_HIGH 202 and MP_HIGH 204 provide high voltage, +HV, to the transmitter output 238. Similarly, stacked drive transistors MN_LOW 206 and MP_LOW 208 provide high voltage, −HV, to the transmitter output 238 when enabled.

The stacked N-type and P-type transistors employed by embodiments of the present disclosure provide a number of advantages. Using an N-type transistor in series with a P-type transistor on both the high and low sides compensates for the lower mobility of the P-type transistor, and results in a smaller circuit area (for example, 15-20% less area) than would be required by an embodiment employing only P-type transistors on one side. Because the characteristics of one transistor type compensate for the characteristics of the other, high/low side symmetry also results in significantly improved performance in less than nominal conditions, for example, at temperature extremes or at process limits. Symmetry can provide a substantial improvement in the harmonic distortion present in the output signal. For example, at the process limits, symmetry can result in as much as a 25% reduction in the second harmonic content of the output with respect to the fundamental when compared to an asymmetrical embodiment.

As explained above, voltage should be predictably distributed across each transistor of a set of stacked transistors. The bias network comprising resistors R0 210, R1 212, R2 214, and R3 216 ensures that voltage is approximately equally distributed across each transistor of transistor pair MN_HIGH 202 and MP_HIGH 204, and each transistor of transistor pair MN_LOW 206 and MP_LOW 208 to assure that the breakdown voltage of the transistors is not exceeded. In some embodiments, for example, the voltage drop across a selected drive transistor may be within 10% of the voltage drop across the other drive transistor of the transistor pair.

As shown in FIG. 2, in embodiments of the present disclosure, the center node 226 of the bias network is preferably grounded. By grounding node 226, embodiments of the present disclosure advantageously decouple the gate drive of transistors MP_HIGH 204 and MN_LOW 206 from the transmitter output 238. Thus, the gates of drive transistors MP_HIGH 204 and MN_LOW 206 are not affected by voltage present on the output 238, and consequently are able to respond more quickly than possible in an embodiment that connects node 226 to transmitter output 238, or couples the control inputs of drive transistors MP_HIGH 204 and MN_LOW 206 in some fashion. The time required for the drive transistors MP_HIGH 204 and MN_LOW 206 to discharge voltage on the nodes 228 and 230 respectively, is one factor determining how quickly the transmitter output 238 returns to zero when transmitter 200 drive is disabled. If MP_HIGH 204 and MN_LOW 206 are slow to discharge nodes 228 and 230, then the voltage on the transmitter output 238 may require a considerable period of time to decay to zero. While connecting node 226 to the transmitter output 238 may help equalize voltage across the bias network, it also serves to degrade gate drive to transistors MP_HIGH 204 and MN_LOW 206 by causing the gates to follow the output 238. By connecting bias network node 226 to ground, embodiments of the present disclosure provide fast discharge of nodes 228 and 230 by the drive transistors MP_HIGH 204 and MN_LOW 206 through transducer 102. Thus, embodiments of the present disclosure can exclude a dedicated transmitter output 238 clamping circuit as required by other embodiments. Consequently, embodiments of the present disclosure advantageously reduce transmitter circuit area and associated cost.

In ultrasound applications, the duty cycle of the transmitter 200 can be low (i.e., the transmitter on time is short relative to the transmitter off time). For example, the transmitter 200 duty cycle may be in the range of 1% (i.e., on 1% of the time and off 99% of the time), so that even though the drive transistors 202, 204, 206, 208 may conduct a relatively large amount of current, the large amount of current is required for only a short period of time.

The high-side driver, comprising MN_HIGH 202 and MP_HIGH 204, is enabled to provide voltage HV to output 238 by asserting signal T1 218 (i.e., bringing the T1 218 signal voltage near HV). Similarly, the low side driver, comprising MN_LOW 206 and MP_LOW 208, is enabled to provide voltage –HV to output 238 by asserting signal T2 220 (i.e., bringing the T2 220 signal voltage near –HV). Either of the high-side or the low-side drivers can be disabled by bringing the corresponding control signal (T1 218 or T2 220) near to ground. Thus, when both the high and low side drivers are disabled, the voltages present on T1 218 and T2 220 are preferably approximately at ground. Consequently, the voltage drop across the bias network comprising R0 210, R1 212, R2 214, and R3 216 can be zero or very small when the transmitter 200 is disabled. By way of contrast, the current flowing in the bias network of a disabled asymmetrical output driver can be on the order of 10 milli-amperes. Such a reduction in quiescent current is significant when the 1% duty cycle of the ultrasound transmitter 200 is considered.

The drive transistors, for example MP_HIGH 204 and MN_LOW 206, can be very large to achieve a low on resistance. Correspondingly, the gate capacitance of large field effect transistors ("FETs") can also be very large. Transmitter 200 preferably comprises buffer drivers 222, 224 to drive the gates of drive transistors MP_HIGH 204 and MN_LOW 206 respectively. The buffer drivers 222, 224 provide current suitable to enable fast switching of the drive transistors MP_HIGH 204 and MN_LOW 206. In some embodiments, the buffers 222, 224 are source followers. Ultrasound transmitter embodiments not incorporating buffer drivers 222, 224 suffer from slower switching of the drive transistors MP_HIGH 204 and MN_LOW 206 and consequently may not provide ultrasonic drive signals at frequencies as high as those produced by embodiments of the present disclosure.

The input capacitance of the buffers 222, 224 is preferably substantially lower than the gate capacitance of the drive transistors MP_HIGH 204 and MN_LOW 206, for example, in some embodiments by approximately a factor of 20 or more. Consequently, in embodiments of the present disclosure, the values of resistors R0-R3 210-216 can preferably be 20 times larger than in an embodiment without the drivers 222, 224. Thus, the current flowing through bias resistors R0-R3 210-216 when the transmitter 200 is active can be 20 times lower than in an embodiment omitting the buffer drivers 222, 224.

An ultrasonic drive signal is generated by transmitter 200 as follows. MN_HIGH 202 and MP_HIGH 204 are turned on and MN_LOW 206 and MP_LOW 208 are turned off to drive the output 238 to +HV. MN_HIGH 202 and MP_HIGH 204 are turned off and MN_LOW 206 and MP_LOW 208 are turned on to drive the output 238 to –HV. Thus, the high and low side drivers are alternately turned on and off at the desired frequency to generate an ultrasonic drive signal on the transmitter output 238. During intervals when no ultrasonic drive signal is being generated, the high and low side drivers are disabled, and the transmitter output 238 returned to zero by bringing T1 218 and T2 220 to ground. In at least some embodiments, the output 238 is returned to zero for an interval between when one driver polarity is disabled and the other is enabled by disabling both drivers for the interval. In some embodiments, a single polarity output is generated by repetitively enabling and disabling a single polarity of driver. For example, by repetitively enabling and disabling MN_HIGH 202 and MP_HIGH 204, and holding MN_LOW 206 and MP_LOW 208 disabled, only positive voltage pulses are generated.

FIG. 3 shows a flow diagram for a method for generating a high voltage ultrasonic drive signal in accordance with various embodiments. Though depicted sequentially as a matter of convenience, at least some of the actions shown can be performed in a different order and/or performed in parallel. Additionally, some embodiments may perform only some of the actions shown. In block 302, the transmitter 200 is producing no ultrasonic drive signal. Consequently, the high-voltage drive transistors MN_HIGH 202, MP_HIGH 204, MN_LOW 206, and MP_LOW 208 are turned off.

If transducer drive is requested, in block 304, then generation of the drive signal proceeds in block 306 where the positive portion of the high-voltage ultrasonic drive signal is generated. +HV drive is enabled by turning on high-side drive transistors MN_HIGH 202 and MP_HIGH 204, and turning off low-side drive transistors MN_LOW 206, and MP_LOW 208.

The negative portion of the high-voltage ultrasonic drive signal is generated in block 308, where –HV drive is enabled by turning on drive transistors MN_LOW 206 and MP_LOW 208, and turning off high-side drive transistors MN_HIGH 202 and MP_HIGH 204.

Embodiments may repetitively perform the operations of blocks 306 and 308 to generate any number of cycles of a high-voltage ultrasonic drive signal. Some embodiments generate a drive signal of a single polarity by omitting the operations of one of blocks 306 and 308 to produce an output signal alternating between ground and either –HV or +HV. In some embodiments, the operation of block 310 is performed between blocks 306 and 308 to provide a zero output between positive and negative drive signals.

In block 310, the desired number of high-voltage cycles have been generated and ultrasonic drive is not required for at least a predetermined time period. The drive transistors MN_HIGH 202, MP_HIGH 204, MN_LOW 206, and MP_LOW 208 are turned off to disable high-voltage drive onto the transmitter output 238, and to advantageously reduce transmitter 200 quiescent power consumption. As explained above the duty cycle of the high voltage transmitter may be approximately 1% in some embodiments, thus reducing current flow in the bias resistors R0-R3 210-216 when the transmitter 200 is disabled can result in substantial power reduction. Moreover, in embodiments of the present disclosure, disabling the transmitter 200 causes the transmitter output 238 to quickly return to zero without aid of a dedicated clamping circuit.

If, in block 312, transducer drive is to be continued, that is, another ultrasonic signal burst is required, then after a predetermined time delay, in block 314, signal generation continues in block 306 as described above.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. An ultrasound transmitter, comprising:
a high side driver and a low side driver, wherein each of the high side driver and the low side driver comprising an N-type field effect transistor (FET) serially coupled to a P-type FET, where, the N-type FET and P-type FET of each of the high side driver and the low side driver configured to switch current to an output of the driver in response to a driver switching control signal;
buffer drivers comprising inputs and outputs where inputs are coupled to the bias network and outputs are coupled to both the high side and the low side drivers;
a bias network that substantially equalizes the voltage drop across the N-type FET and the P-type FET of the high side and the low side drivers; wherein the bias network further comprises:
a first, second, third and fourth resistance coupled in series between a high side driver input and a low side driver input on an input side of the ultrasound transmitter,
wherein the high side buffer is coupled between the first resistance and the second resistance and the gate of the high side P-type FET;
wherein the low side buffer is coupled between the third resistance and the fourth resistance and the gate of the low side N-type FET; and
wherein a node between the second resistor and the third resistor is coupled to a node between the high side buffer and the low side buffer, and the high side buffer and low side buffer are coupled to ground;
wherein current flow through the bias network becomes substantially zero when the first and second drivers are disabled; and
wherein activation of the high side driver drives the ultrasound transmitter output to a first voltage and activation of the low side driver drives the ultrasound transmitter output to a second voltage, said activations producing a high voltage ultrasonic drive signal at the ultrasound transmitter output preserving a symmetry of the high-side and the low-side.

2. The ultrasound transmitter of claim 1, wherein the ultrasound transmitter output voltage is not fed back into the first bias network.

3. The ultrasound transmitter of claim 1, wherein the high side driver drives a positive voltage to the ultrasound transmitter output.

4. The ultrasound transmitter of claim 1, further comprising the buffer driver coupled between the bias network and a drive transistor of the high side driver.

5. The ultrasound transmitter of claim 1, wherein the control inputs of the high side driver are decoupled from the driver switching control inputs of the low side driver.

6. The ultrasound transmitter of claim 1 wherein a node of the bias network is grounded.

7. The ultrasound transmitter of claim 1, wherein the ultrasound transmitter comprises no clamping circuit that brings the ultrasound transmitter output to ground when the high-side and low-side drivers are disabled.

8. The ultrasound transmitter of claim 1, wherein the low side driver drives a negative voltage onto the ultrasound transmitter output.

9. An ultrasound imaging system, comprising:
an ultrasonic signal transducer that converts an electrical signal into an acoustical signal;
a signal transmitter coupled to the transducer, the transmitter comprising a high-side driver that comprises a first set of stacked complementary drive transistors and a low side driver that comprises a second set of stacked complementary drive transistors, each driver comprising an N-type field effect transistor (FET) serially coupled to a P-type FET, the N-type FET and the P-type FET of each high side and low side driver configured to switch current to an output of the driver in response to a common driver switching control signal; and
a high side buffer and a low side buffer;
a bias network that substantially equalizes the voltage drop across the N-type FET and the P-type FET of the low side driver and the high side driver, wherein the current flow in the bias network is reduced to zero by disabling the high-side and the low-side drivers,
wherein the bias network further comprises:
first, second, third and fourth resistance coupled in series between a high side input and a low side input on an input side of the ultrasound transmitter,
wherein the high side buffer is coupled between the first resistance and the second resistance and the gate of the high side P-type FET;
wherein the low side buffer is coupled between the third resistance and the fourth resistance and the gate of the low side N-type FET; and
wherein a node between the second resistor and the third resistor is coupled to a node between the high side buffer and the low side buffer, and the high side buffer and low side buffer are coupled to ground;
wherein activation of the high side driver drives the ultrasound transmitter output to a first voltage and activation of the low side driver drives the ultrasound transmitter output to a second voltage, said activations producing a high voltage ultrasonic drive signal at the ultrasound transmitter output preserving a symmetry of the high-side and the low-side.

10. The ultrasound imaging system of claim 9, wherein disabling the high-side driver and the low-side driver reduces current flow in the bias network to zero.

11. The ultrasound imaging system of claim 9, wherein the bias network is decoupled from the ultrasound transmitter output.

12. The ultrasound imaging system of claim 9, wherein driver switching control of the high-side driver and the low-side driver is decoupled from the ultrasound transmitter output.

13. The ultrasound imaging system of claim 9, wherein each of the high side driver and the low side driver comprises a pair of stacked complementary drive transistors.

14. The ultrasound imaging system of claim 9, wherein ultrasound transmitter output current flows through an N-type FET to a P-type FET of the high side driver, and through the P-type FET to the ultrasound transmitter output.

15. The ultrasound imaging system of claim 9, wherein ultrasound transmitter output current flows from the ultrasound transmitter output through an N-type FET to a P-type FET on the low side driver.

\* \* \* \* \*